United States Patent [19]
Christensen et al.

[11] Patent Number: 5,978,435
[45] Date of Patent: Nov. 2, 1999

[54] METHOD AND AN APPARATUS FOR DETERMINING THE NUMBER OF PARTICLES OR CELLS IN A LIQUID SAMPLE

[75] Inventors: Steen Kold Christensen, Virum; Christian Born, Holte; Tove Asmussen, Farum; Mogens Bering Larsen, Helsinge, all of Denmark

[73] Assignee: Foss Electric A/S, Hillerød, Denmark

[21] Appl. No.: 08/983,043

[22] PCT Filed: Aug. 20, 1996

[86] PCT No.: PCT/DK96/00351

§ 371 Date: Jan. 15, 1998

§ 102(e) Date: Jan. 15, 1998

[87] PCT Pub. No.: WO97/07390

PCT Pub. Date: Feb. 27, 1997

[30] Foreign Application Priority Data

Aug. 21, 1995 [DK] Denmark .................................. 0932/95

[51] Int. Cl.[6] ................................................. G06M 11/02
[52] U.S. Cl. ................................ 377/10; 377/12; 364/555
[58] Field of Search ............................. 364/555; 377/10, 377/12

[56] References Cited

U.S. PATENT DOCUMENTS 4,021,117  5/1977  Gohde et al. .............................. 356/39
4,667,335  5/1987  Deindoerfer .............................. 377/10

FOREIGN PATENT DOCUMENTS 0342501  11/1989  European Pat. Off. .
2812470   3/1979  Germany .
1105136   3/1987  Japan .

OTHER PUBLICATIONS

Skoog, D. A., "Principles of Instrumental Analysis," Saunders Golden Sunburst Series, Edition 3 (1984) pp. 1–25.

English language Abstract for Japanese Patent Publication 1–105136 A dated Mar. 20, 1987.

*Primary Examiner*—Margaret R. Wambach

[57] ABSTRACT

A method and apparatus for determining the number of particles or cells in a liquid sample. The method comprises a) determining the number of particles or cells in a first volume of the liquid sample, b) determining the statistical uncertainty of the determined number of particles in said first volume, c) if the determined uncertainty is larger than a pre-determined value, determining the number of particles or cells in a further volume of the liquid sample, d) adding the numbers of cells or particles determined in steps a) and c), e) determining the statistical uncertainty of the number of particles determined in step d), f) repeating steps d) and e) with a further volumes of the liquid sample, until the uncertainty determined in step e) is lower than said pre-determined value or until a pre-determined total volume of the liquid sample in which the number of cells or particles has been determined exceeds a pre-determined volume being larger than said first volume. In this way, the volume examined and the uncertainty of the measurement may be selected so that a suitable compromise between the uncertainty and the time required to perform the measurement can be obtained. The apparatus according to the invention comprises a liquid flow system allowing the measurement sequence to be interrupted as soon as the calculating means decide that the uncertainty of the actual cell count is small enough to rely on the present determination. The apparatus will then be ready to carry on with the next sample, thereby maintaining a high capacity while obtaining reliable cell counts.

32 Claims, 7 Drawing Sheets

Fig. 5
a) 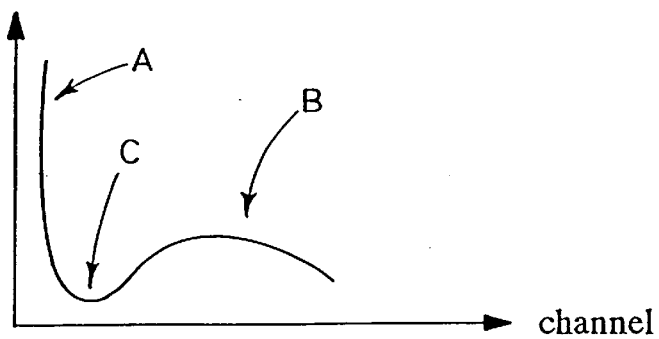
b) 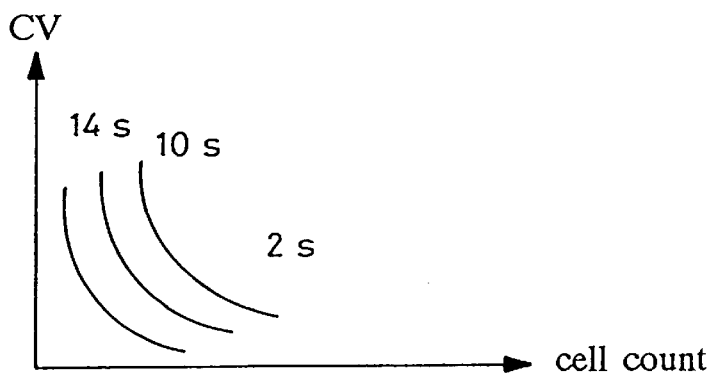
c) 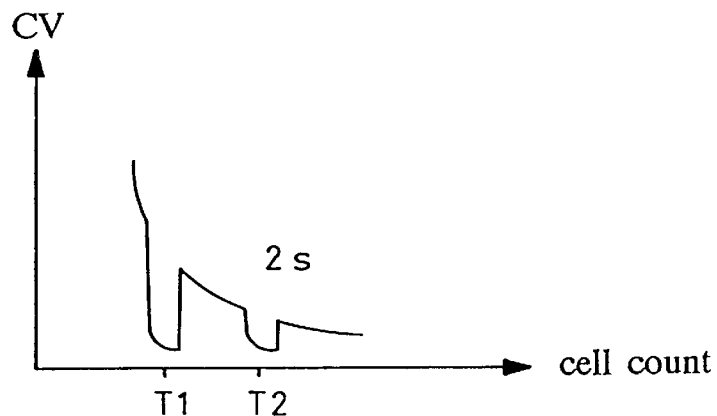
d) 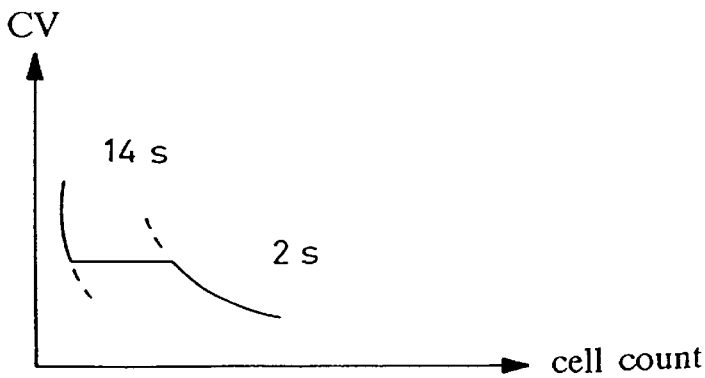

METHOD AND AN APPARATUS FOR DETERMINING THE NUMBER OF PARTICLES OR CELLS IN A LIQUID SAMPLE

This application is the national phase under 35 U.S.C. §371 of prior PCT International Application No. PCT/DK96/00351 which has an International filing date of Aug. 20, 1996 which designated the United States of America, the entire contents of which are hereby incorporated by reference.

TECHNICAL FIELD

The present invention relates to counting particles or cells in liquid samples and in particular in connection with flow cytometry, which is a widely used technique for determining e.g. the number of somatic cells in milk samples.

BACKGROUND ART

In typical flow cytometers, the determination procedure is a simple counting procedure where a part of a milk sample is mixed with dye and the number of cells therein is counted using e.g. a fluorescence measurement.

The uncertainty of a measurement can be expressed by the standard deviation (cf. D. A. Skoog 'Principles of instrumental analysis', Saunders College Publishing, Philadelphia, U.S.) e.g. the relative standard deviation, also called the coefficient of variation, "CV". The 'CV' of a value determined by a counting procedure will depend on the number counted. For a typical Poisson distribution the 'CV' is inversely proportional to the square of the number counted, Thus, the uncertainty of a large number of particles or cells, e.g. somatic cells in milk will be smaller than the uncertainty of a small number of cells.

In typical, known flow cytometers, this is not taken into account. In these instruments, the number of cells is determined in a pre-determined volume of a milk/dye mixture. However, in some instruments, this is taken into account by performing an alternative measurement by detecting a pre-selected number of cells and by determining the volume in which this number of cells are present. Cell counting is also performed using techniques other than flow cytometry. Manual cell counting is often performed on human blood. In this technique, the cells in a pre-selected volume of the blood are counted. Alternatively a volume of blood containing a predetermined number of cells may be measured.

The above two methods have the disadvantages that they in a sense are static. Either the uncertainty is the same for all measurements or it is allowed to drift for all measurements. Therefore, there is a risk of obtaining results having a large uncertainty. The solution to this is to either increase the volume examined in order to count more particles or cells or to use the alternative method using a predetermined number of cells and therefore a pre-selected uncertainty. By this method, however, the measurement procedure may for some samples take an unacceptably long period of time.

SUMMARY OF THE INVENTION

The present invention provides a solution to this problem by providing a measurement where the uncertainty is "dynamic" (i.e. variable). The uncertainty may be selected dependently or independently of the results of the measurement.

In fact, in a first aspect, the present invention relates to a method of determining the number of particles or cells in a liquid sample, the method comprising:

a) determining the number of particles or cells in a first volume of the liquid sample, b) determining the statistical uncertainty of the determined number of particles in said first volume, c) if the determined uncertainty is larger than a pre-determined value, determining the number of particles or cells in a further volume of the liquid sample, d) adding the numbers of cells or particles determined in steps a) and c), e) determining the statistical uncertainty of the number of particles determined in step d), f) repeating steps d) and e) with (a) further volume(s) of the liquid sample, until the uncertainty determined in step e) is lower than said pre-determined value or until a predetermined total volume of the liquid sample in which the number of cells or particles has been determined exceeds a pre-determined volume being larger than said first volume.

In this way, the volume examined and the uncertainty of the measurement may be selected so that a suitable compromise between the uncertainty and the time required to perform the measurement can be obtained.

Naturally, there are different ways of expressing a statistical uncertainty depending also on the determination in question. Thus, if the uncertainty is expressed as the relative standard deviation (CV), this uncertainty is proportional to the inverse of the square of the counted number.

In the present invention, the uncertainty is evaluated a number of times during the determination, in order to not unnecessarily continue the determination after the point in time at which a suitable uncertainty has been reached. In this way, the determination is performed substantially as fast as possible and still with an uncertainty acceptable to the operator or user.

Naturally, in order to ensure a certain minimum sample capacity (measured samples per hour) of an apparatus incorporating the method of the invention, practical considerations may require that the determination is only allowed to run for a given maximum period of time. Alternatively, the total volume of the liquid sample wherein the number of particles or cells may be determined, may be limited to a given maximum volume. Especially in apparatuses for milk analysis, the capacity of an apparatus is important as the total number of samples to be tested per day may easily be several thousand.

Even though the number of particles or cells in a volume of a liquid sample may be determined in a number of ways incorporating the method of the invention, it is presently preferred that the number of cells or particles in the first and subsequent volumes is determined by flowing said volumes past a detector detecting the presence of the cells or particles.

Preferably, the cells or particles are stained with a fluorescing agent and irradiated with radiation exciting the fluorescing agent. The detector may detect the presence of the particles or cells by detecting the fluorescence emitted from the excited agent.

Usually, the emission of the fluorescence takes place almost instantaneously after excitation of the fluorescing agent. Therefore, it is preferred that the irradiation with radiation exciting the agent and the emission of the fluorescence takes place while the irradiated cells or particles are held by a cuvette made of a material transmitting both the radiation and the fluorescence. An alternative way of detecting cells or particles in a stream of liquid is to use a technique where the particles or cells are irradiated by e.g. a laser and where light scattered by the particles or cells is detected.

A second alternative method of determining the number of cells or particles in a liquid sample is one where the detector detects the presence of the cells or particles by detecting a difference in the electrical conductivity of the volumes flowing past the detector. This is e.g. the method used in so-called Coulter counters.

In addition, the determination of the number of particles or cells in the first and subsequent volumes may alternatively comprise an assay step which is based on the quantification of a target molecule or of a molecular interaction involving a target molecule, the interaction itself or a product thereof being detectable and being correlated to the number of cells or particles in the volumes.

Naturally, substantially all types of immunological assays may be used in connection with the present invention as they may be used for the determination of the presence and/or quantity of target molecules on the cells or particles. These types of assays comprise a large number of different detection methods such as the detection of the resulting radioactivity of the liquid sample or the fluorescence, pH or colour thereof. In these types of assays, the agent may be a colouring agent colouring the cells or particles, whereby the determination of the number of cells or particles in the volumes may be performed by determining the coloration of the volumes.

The cells or particles and the agent may take part in an antigen/antibody reaction. The agent, which has taken part in the antigen/antibody reaction, may be able to direct a chemical reaction in the volumes either starting and taking part in this reacting, or simply acting as a catalyst therein.

One type of agent performing this type of reaction is the type typically seen in e.g. ELISA assays. Thus, the agent may comprise an enzyme, where the chemical reaction may be the enzymatic splitting of a reagent. The concentrations of the reaction product(s) from the enzymatic splitting of the reagent relate to the number of cells or particles in the volumes—so that the determination of the concentration of the reaction product(s) will form the basis for at determination of the number of cells or particles in the liquid sample.

By a first preferred method according to the invention the pre-determined value is independent of the determined number of cells. This means that the uncertainty obtained in the determinations is better than or equal to the same value independently of the number of cells or particles determined—taking into account a practical limitation on the maximum available measurement time or volume.

By the second method according to the invention the pre-determined value depends on the determined number of cells. The second method may be preferred when it is desired to mainly determine whether the number of cells or particles in the sample is positioned above or below a given threshold value. Here, a large uncertainty may be tolerated, if it is certain that the determined number of cells or particles is correspondingly far away from the threshold value. Then, if the number of cells or particles in the sample is evaluated to be close to the threshold value, a lower uncertainty will be desired to determine whether the determined number of cells or particles is, in fact, above or below the threshold value.

Thus, in the second method, it may be preferred that the pre-determined value is reduced in pre-determined intervals of numbers of cells or particles and typically in intervals centered around threshold values used for e.g. payment purposes in the milk industry.

Usually, these intervals will be defined by an upper and lower cell or particle number, each being in the interval, and it may be preferred that the reduced pre-determined value is reduced by at least 10%, such as at least 20%, preferably at least 30%, such as at least 40%, preferably at least 50%, compared to that of the cell or particle numbers adjacent to the upper and lower cell or particle numbers and outside the interval.

Alternatively, according to the second method, the probability of correct classification may be determined, when the number of cells or particles has been determined. In this connection, the probability of correct classification may be the probability of the determined number of cells or particles being on the correct side of a given threshold value. If this probability is high enough, the measurement may be stopped. If not, the measurement may be continued, and a new, larger total number of cells or particles may be determined and a new, larger probability of correct classification may be calculated.

According to a preferred method of determining the number of cells or particles in the sample the number of cells or particles of the first and subsequent volume(s) of the liquid sample is determined while the first and subsequent volume(s) of sample are flowing through the cuvette. This method has the advantage that the flow of the liquid may be so thin that substantially only one cell or particle may be detected at a time.

Specifically, according to a more preferred method the liquid sample flows in a single, thin string or layer surrounded by a sheath fluid inside the cuvette. This is the case in flow cytometry, for example.

This method has the advantage that impurities present in the liquid and having a size larger than the particles or cells and the size of the string/layer of liquid sample will not cause clogging as they might do if flowing in a narrow liquid channel. In the above preferred method, the channel may be made wider—thanks to the sheath fluid—so that any impurities may be transferred through the channel without causing clogging. The cross section of the actual flow of the liquid sample should be kept small as the measuring area "covered" by the detector may be kept correspondingly small. It is preferred that substantially only one cell or particle may then be present in the measuring area at a time.

The method according to the invention is preferably applied for determining the number of cells in a sample of milk or a milk product. In methods of this type, the presently preferred agent or dye is Ethidium Bromide.

In a second aspect, the present invention relates to an apparatus for determining the number of particles or cells in a liquid sample, said apparatus comprising:

means for determining the number of particles or cells in a first and (a) further volume(s) of the liquid sample, means for determining the statistical uncertainty of the determined number of particles or cells in a given volume of said liquid sample, means for determining whether the determined uncertainty is lower than a predetermined value, and means for adding the numbers of particles or cells determined in the first and the further volumes of the liquid sample.

As described above, an apparatus of this type has the advantage over the prior art apparatuses that a compromise may be made independently in each measurement between the uncertainty of the measurement and the time required to obtain the measurement.

It is preferred that the apparatus according to the invention comprises means for holding the first and subsequent volume(s) of the sample during the determination of the number of cells or particles therein, i.e. further volumes of the same sample can be introduced continuously until the desired uncertainty is reached.

Several techniques may be used to determine the number of cells or particles in a liquid. Some of these techniques comprise staining the cells or particles and subsequently detecting cells or particles stained with the dye. These methods may have the advantage that the dye may be chosen to be specifically targeted for the cells or particles in question. Thereby impurities will be less prevalent compared to e.g. a scatter measurement where impurities and cells or particles may not be distinguishable.

In the present apparatus, the means for determining the number of cells or particles in the first and subsequent volume(s) of sample preferably comprise means for mixing at least part of the liquid sample with a volume of a dye so as to stain the cells or particles with a fluorescing agent, means for irradiating the stained cells or particles with radiation exciting the fluorescing agent, and means for detecting fluorescence emitted from stained cells or particles having been irradiated with the exciting radiation.

Obviously, in an alternative apparatus, instead of a fluorescing agent the dye may comprise an agent colouring the mixture or catalyzing a process, which itself or a result thereof may be detected. Such process can be a chemical process, and a detectable result can be a resulting product. In addition, the so-called Coulter-principle of measuring particles or cells in a liquid may be used in connection to the present invention. According to this principle, the liquid is passed through a thin tube or the like provided with measuring electrodes, arranged to measure the electrical conductivity in the liquid passing the electrodes. The particle or cell is detected as its electrical conductivity differs from that of the liquid.

The means for holding the first and subsequent volume(s) of the sample during the determination of the number of cells or particles therein preferably hold these volumes during irradiation thereof with the exciting radiation and during emission of the fluorescence. These holding means preferably comprise a cuvette transmitting at least part of the exciting radiation and the fluorescence.

The apparatus according to the invention preferably also comprises means for storing a number of pre-determined values, and means for selecting a pre-determined value depending on the number of cells or particles determined in the liquid sample.

As described above, the present apparatus may preferably operate in one of two modes. In the first mode, the uncertainty desired is chosen to be independent of the number of cells or particles determined. In the second mode, the uncertainty desired depends on the number of cells or particles determined in the liquid sample.

As the dyes, such as Ethidium Bromide (EB), which are typically used in determinations of cells in milk samples are mutagenic and potentially carcinogenic, the disposal of liquid sample contaminated with dye should typically be obtained through a processing station, as liquids having a concentration above a given threshold may not be disposed of directly in sewers, for example.

To this end, the present apparatus preferably comprises waste means for receiving the mixture of dye and liquid sample subsequent to the determination of the number of cells or particles in the sample. In fact, the waste means of the present apparatus preferably comprise at least two containers for receiving different parts of the mixture, a first container for receiving parts of the mixture where the concentration of dye is lower than a pre-selected concentration and a second container for receiving parts of the mixture where the concentration of dye is higher than the pre-selected concentration. In this way, the first container receives only parts of the mixture having a low dye concentration, allowing these parts to be disposed of in a sewer, for example. This means that not all of the mixture has to be disposed of at processing stations usually requiring payment for the disposal. Separating the waste of the apparatus provides both reduced costs for the owner of the apparatus and reduces the incentive for "accidental" illegal dispose of the dye in a manner polluting the environment.

In the case where the liquid sample is a milk sample, even disposal of volumes of pure milk sample must in certain areas be achieved through processing stations. Therefore, the present apparatus preferably further comprises waste means for receiving parts of the liquid sample which has not been mixed with the dye. Accordingly, the waste of the apparatus may be separated into non-polluted, slightly polluted and heavily polluted parts. The pollution threshold values separating these parts may be chosen freely, so that the instrument may be adapted to the regulations of the area in which it is to be used.

Another "problem" or point to take into account when using health hazardous dyes is the handling thereof by the operator or laboratory personnel when preparing this dye and introducing it into the apparatus. Typically, Ethidium Bromide is prepared from a powder which is dissolved in distilled water, to which citric acid and Triton™ is added. This operation, naturally, imposes a health hazard to the person performing it.

Therefore, the present apparatus, when utilizing hazardous dyes, preferably uses pre-dissolved and concentrated dyes. These dyes are automatically diluted in the apparatus thus comprising a mixing means connected to a concentrated dye container and a dilute container and having an exit from which the diluted dye, ready for use, is output, and from which the dye may be transferred to other parts of the apparatus. In this way, laboratory personnel are not required to actually handle the EB but merely change the concentrated dye containers.

However, even this operation may expose the operator or laboratory personnel to health hazards. Certain types of containers cannot be totally emptied, whereby small amounts of dye will be left in or on the container or the surrounding parts of the apparatus. Another equally grave problem is the fact that piercing a new container may bring about squirting of the contents of the container due to pressure difference inside and outside the container.

In order to solve these problems, the concentrated dye container is preferably a resilient container, whereby pressure equalization automatically takes place so that squirting may be avoided. Furthermore, if the resilient container is of the type used for infusion liquids in hospitals, these containers may be substantially totally emptied. These containers furthermore have the advantage that no parts of the contents can escape the container except through a syringe penetrating the rubber interface thereof. Subsequent to retraction of the syringe, dye is only present on that syringe. Protection of this syringe during interchange of containers may be performed in a number of ways, one of which is illustrated in the figures. Thus, the preferred apparatus, apart from presenting a solution to the uncertainty/measuring time problem, presents features highly appreciated by the operators from both an economic point of view, an environmental point of view and a health hazard point of view.

BRIEF DESCRIPTION OF THE DRAWINGS

FIG. 5 illustrates four graphs related to the different modes of function of the instrument.

DETAILED DESCRIPTION OF A PREFERRED EMBODIMENT

Figure 1:
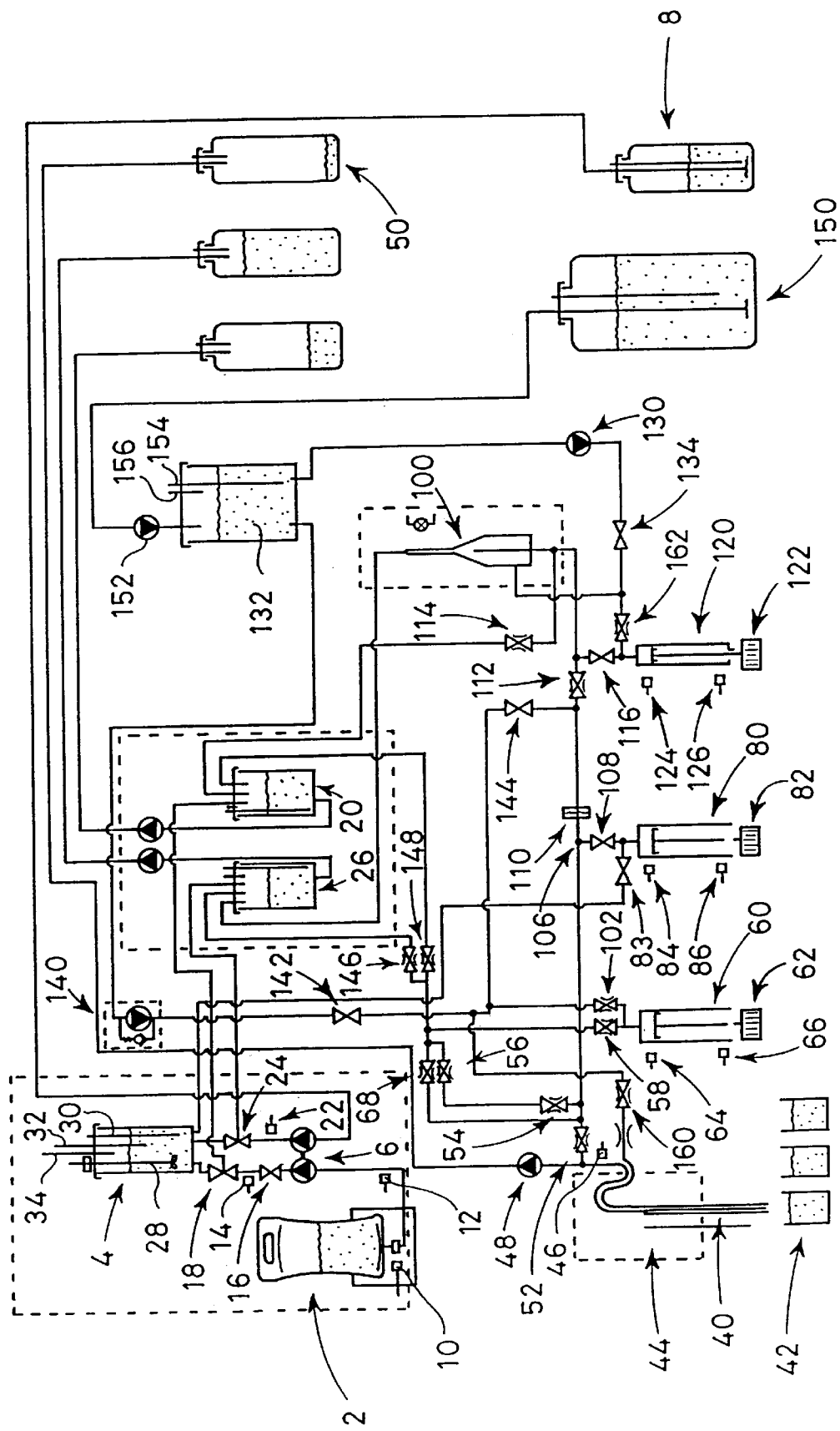
FIG. 1 illustrates the flow of liquids in a preferred embodiment of an apparatus according to the invention.

In the following, a preferred embodiment of the present invention incorporated in an apparatus for determining the number of cells in milk samples will be described with reference to the drawings. FIGS. 1–7 illustrate the overall operation and flow of liquids in the presently preferred embodiment of an apparatus according to the invention, a so-called cell counter. A typical application of the cell counter is counting somatic cells in raw milk. Preferably, cell counters shall be able to handle about 500 milk samples per hour. A low cell count indicates a high grade raw milk, for which the milk producer shall be paid a high milk price. A high cell count indicates a low grade raw milk, for which the milk producer shall be paid less. Generally a high grade price will be paid for raw milk having a cell count below a first predefined value i.e. a 'first grade limit'. A medium price will be paid for raw milk having a cell count between the first predefined value and a second predefined value or 'second grade limit'. A low grade price will be paid for raw milk having a cell count above the second predefined value. Therefore, a knowledge of the cell count is important. Specifically, when the cell count is close to one of the predefined values, which are decisive for the payment, it is important to determine with a high degree of probability whether the cell count is below or above the predefined values or 'grade limits'.

The present cell counter (FIG. 6) operates by means of the so-called flow cytometry technique where the liquid comprising the particles or cells to be detected is introduced inside a carrier liquid as a sheathed flow into a cuvette in which the liquids are exposed to a typical epi-fluorescence measurement.

In order to prepare the cells of the sample for the fluorescence measurement the milk is mixed with a dye solution comprising Ethidium Bromide (EB), which is a DNA-specific colouring agent, as well as chemicals for dissolving the cell walls in order to bring the EB in contact with the DNA of the cells. Subsequently, the stained cells are transferred to the flow cytometer cuvette where the fluorescence measurement takes place.

The EB is contained in a bag. The concentration of the EB is 10 times higher than the concentration required for mixing with the milk in the apparatus. This EB input 2 will be further described in connection with FIG. 2. From the EB input 2, EB is pumped to a mixing chamber 4 by one pump of a tandem pump 6, of which the other pump transfers diluent liquid from a diluent liquid container 8 to the mixing chamber 4. The present tandem pump 6 is adapted to dilute the EB by a factor of 10. A sensor 10 detects whether a bag is present in the bag container and whether this container is closed. Liquid sensors 12 and 14 detect the presence of EB along the path from the EB input 2 to the mixing chamber 4. A normally closed valve 16 ensures that EB does not pass when the instrument is not in operation.

To ensure the desired dilution of the EB (by the factor of 10), a well-defined amount of EB must be transferred to mixing chamber 4 as well as a well-defined amount of diluent liquid. Therefore air should be avoided in the liquid paths. Typically, air might be present if the path from the EB input system 2 to the mixing chamber 4 has been emptied. If air is present this is detected by a liquid sensor 14, controlling a switch 18 adapted to transfer the air-filled EB to a high concentration waste container 20. When the path again is filled with concentrated EB the switch will transfer the concentrated EB to the mixing chamber 4. In a similar way, an optical sensor 22 will detect air in the flow of diluent liquid and subsequently control a switch 24 in order to transfer this air-filled liquid to a low concentration waste container 26. In the mixing chamber 4, a mixer 28 operates when the tandem pump 6 is in operation in order to mix the added chemicals. In addition, in this chamber 3 optical sensors 30, 32 and 34 are present. If sensor 30 does not detect liquid, the apparatus will be put into standby mode. If sensor 32 does not detect liquid, the tandem pump 6 will be activated in order to add liquid to the mixing chamber 4. Subsequently, the sensor 34, when detecting liquid, will stop the operation of the pump 6.

Introduction of a Milk Sample

Figure 6:
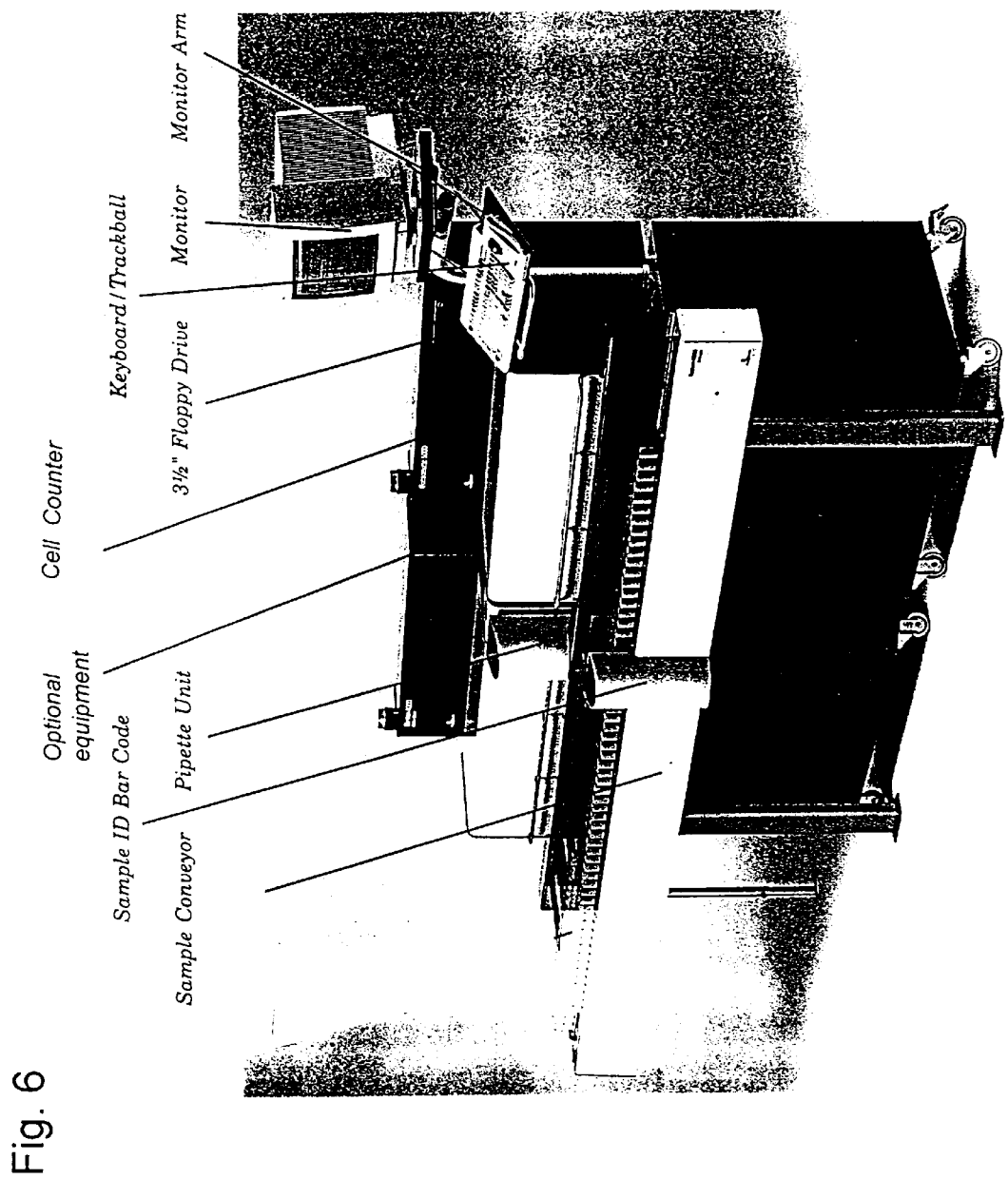
FIG. 6 shows a preferred embodiment of an apparatus according to the invention and FIG. 7 shows a diagram of an example of the calculations performed during the measurements.

In the preferred embodiment the milk samples are arranged in small sample containers 42 in a row on a conveyer (shown in FIG. 6). In an alternative embodiment the containers 42 may be arranged on a rectangular table.

Milk samples are introduced into the present apparatus through a typical pipette 40, which is lowered into one of the sample containers 42 comprising a milk sample. A liquid sensor 44 is immersed along with the pipette 40 in order to ensure that there is, in fact, a liquid sample to be introduced into the apparatus. The preferred pipette 40 is of a well-known type which comprises two coaxial tubes where the sample, when introduced into the apparatus, is sucked through the inner tube into the apparatus.

In the following it is assumed that the pipette has been lowered into a new sample container 42 in order to let a new milk sample be introduced into the instrument.

Through the operation of a pump 48, the pipette 40 is flushed with milk from the new sample container to ensure that the milk being introduced through the pipette 40 is representative of the milk sample in the container 42, i.e. to avoid "carry over" from the preceding milk sample. The flushed milk is directed towards a milk waste container 50. A liquid sensor 46 will detect the presence of liquid. When a given volume of the milk has been transferred into the system, the pump 48 is stopped.

A syringe pump 60 is controlled by a step motor 62 and two optical detectors 64, 66 which sense the position of the plunger through an element (not shown) connected to the plunger of the pump 60. The plunger of the syringe pump 60 is displaced downwards so as to suck liquid into the pump 60 through the path comprising open valves 58, 56, 54, 52. It should be noted that the syringe pump 60 and the liquid path from pump to valve 56 is filled rinsing liquid acting as a "buffer" between the milk samples and the pump 60. It is constantly ensured that no parts of the milk sample enter the syringe pump 60. It is always ensured that only rinsing liquid is present in the pump 60 in order to prolong the life time of the plunger of the pump 60. This also reduces the risk of carry-over between subsequent samples. In fact, the valve 58 is only closed and valve 102 is only open during starting up of the instrument so as to transfer rinsing liquid to the pump 60.

In this way, milk is transferred from container 42 through pipette 40 and into the liquid path between the valves 52, 54, and 56. After a period of time, i.e. when that the milk sample has reached the valve 56, valves 54 and 56 are closed and valve 68 is opened to allow further transfer of milk in a parallel path between the valves 52 and 68.

An advantage of the two parallel liquid paths between valve 52 and valves 56 and 68, is that a larger volume of milk may be introduced before the representative volume is drawn from the sample container 42. This is required when the apparatus has a long liquid path from the pipette 40 to valve 52. This is the case when sample containers 42 are positioned on a table and the pipette movement is controlled by a XY-table as known to one of ordinary skill in the art.

Mixing

Parallel to the introduction of the milk sample into the instrument, diluted EB is transferred from mixing chamber 4 into a syringe pump 80 by opening a valve 83. The pump 80 is driven by step motor 82 and is controlled on the basis of signals from two optical detectors 84 and 86.

In order to precisely control the amount of liquid subsequently dispensed from pump 80, the electronics controlling this pump 80 are reset when the optical detector 84 detects a plunger element (not shown) connected to the plunger of the pump 80. In the same way, in order to control the amount of liquid dispensed from pump 60, the electronics controlling this pump 60 are reset when the optical detector 66 detects the corresponding plunger element (not shown).

Now the milk in the path between valves 52 and 68 shall be mixed with the EB solution in order to stain the cells in the milk sample. The pump 60 is operated to dispense liquid through valve 58 backwards through valve 68, thereby forcing the newly introduced milk sample, contained in the path between the valves 68 and 52, towards a mixing point 106 on the path between the pumps 60, 80 and the cuvette 100. With a slight delay, the pump 80 is operated to transfer diluted EB from pump 80 through an open valve 108 to the mixing point 106. At this point the liquid dispensed from pump 80 is actually mixed with the milk contained between valves 68 and 52. The mixture is passed through a filter 110 and an open valve 112 in a direction towards the cuvette 100. The path from the mixing point 106 to the cuvette 100 allows the two mixed liquids to incubate in order to ensure correct staining of the cells.

To avoid carry-over the path is flushed with the first portion of the new sample mixture, which is discharged through an open valve 114 into the high concentration waste chamber 20. As the pressure inside the cuvette 100 is typically slightly higher than the atmospheric pressure, it is expected that also a small part of the sheath liquid (also called carrier liquid) therein is sucked towards the waste chamber 20.

Parallel to this procedure, a third syringe pump 120 is operated by a step motor 122 displacing its plunger to a lower position detected by a optical sensor 126 in order to suck rinsing liquid from a container 132 via pump 130 through a now open valve 162.

Having ensured that the liquid positioned between the valves 112 and 114 is representative of the new sample mixture, valves 112 and 114 are closed, and a valve 116 is opened. Subsequently, the pump 120 is operated in order to transfer liquid from pump 120 into the liquid path between valves 112 and 114, towards the cuvette 100. This operation will force the milk sample mixture from the path between the valves 112 and 114 into the inner liquid tube of the cuvette 100 (See FIG. 3) in the manner known in flow cytometry. Simultaneously, a sheath fluid pump 130 is operated to transfer a carrier or sheath fluid from the rinsing and sheath fluid chamber 132 through an open valve 134 to the outer liquid tube of the cuvette 100 (See FIG. 3). From the cuvette 100, the liquid is passed to the low concentration waste chamber 26. Optionally, a period of time may be allowed to lapse between closing the valves 112 and 114 and until the operation of the pump 120 begins in order to prolong the incubation time.

Measurement of the Number of Cells in the Sample

The actual measurement (the cell counting) of the stained cells is performed by optical/electrical equipment description below during the operation of the pumps 120 and 130, i.e. during the transfer of the mixture comprising the stained cells through the cuvette 100. In the preferred embodiment the measurement is performed by detecting the fluorescence occurring each time a stained cell pass through the cuvette 100.

When the mesurement of a sample is completed, the pump 120 can be reset and the plunger thereof should be positioned at a top position detected by the optical detector 124 in order for the pump 120 to be ready for the next measurement sequence. As it is ensured that no milk (only rinsing liquid) is introduced into in the pump 120, no specific cleaning is required.

Cleaning Procedure

The cleaning of the present instrument takes place at different positions at different times depending on which parts of the instrument are in operation. Thus, when the actual measurement is performed in the cuvette 100, the other parts of the instrument may easily be cleaned and milk from a subsequent milk sample may be introduced into the system. Thus, the parts of the apparatus connected with the pumps 80 and 60 is cleaned by operating a pump 140 which transfers rinsing liquid from the container 132 through a stop valve 142 and through a valve 144 to a position between pumps 60 and 80 and the valve 112. Cleaning liquid is introduced at this point in order to backflush the filter 110 and to introduce liquid through the valves 54, 56, and 68, when valve 52 is closed. The stop valve 142 only ensures that liquid is not introduced into the system unattendedly. Before the input of each new sample rinsing liquid is introduced into the pipette 40 between the two coaxial tubes. By a simultaneous suction the rinsing liquid is sucked through the inner tube and back into the apparatus. In this way, both the outer and inner surfaces of the inner tube are cleaned.

Separation of the Waste

The waste which is discharged from the instrument, may be separated according to the amount of EB comprised in the different portions thereof. To this purpose two valves 146 and 148 are provided, which each close or open a path between the valves 56 and 68 and the containers 26 and 20, respectively. Thus, as the first part of the liquid transferred to the valves 146 and 148 will comprise large amounts of EB, valve 148 will be opened the first 1⁄3 of the total cleaning time so as to transfer the first 1⁄3 of the total amount (i.e. the amount transferred to waste containers 20 and 26) through this path to the high concentration waste chamber 20. Subsequently, valve 148 is closed and valve 146 is opened in order to transfer the rest of the amount to the low concentration waste chamber 26.

The setup illustrated in FIG. 1 further comprises a number of elements intended for the convenience of the operator.

Preferably, it is ensured that the instrument can operate for at least 10 minutes allowing the operator to replace containers of diluent liquid, rinsing and sheath liquid or concentrated EB without having to interrupt the operation of the apparatus.

This is obtained by ensuring that the amount of EB mixture contained in the mixing chamber 4 between the positions at which optical sensors 34 and 32 detect liquid corresponds to the amount used during at least 10 minutes of normal operation. In addition, the rinsing and sheath liquid container 132 is preferably a container which is frequently refilled with liquid from a larger container 150 by operating a pump 152.

The container 132 comprises two optical sensors 154 and 156. When detector 156 detects no liquid, the pump 152 is operated for a given period of time sucking liquid from a container 150. The amount of liquid in the container 132 preferably corresponds to what is used during at least 10 minutes of normal operation. If no liquid is transferred by pump 152, liquid for at least 10 minutes of operation is still present and the operator is warned of the situation. Detector 154 is a safety detector. The instrument is put on stand-by, if the detector does not detect liquid.

Figure 4:
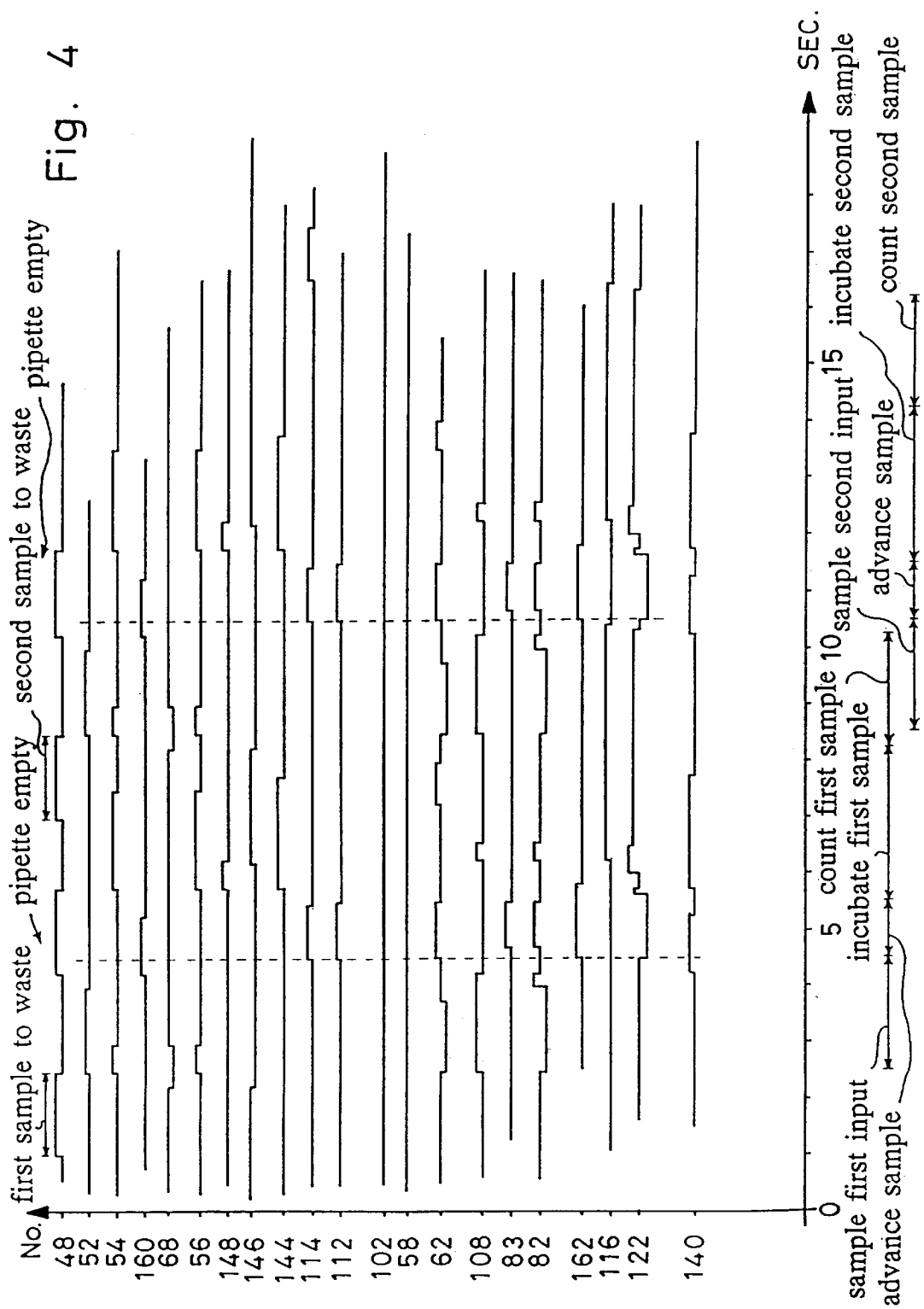
FIG. 4 illustrates a timing diagram of the elements of the apparatus when performing an operation of the type described below.

The preferred timing of the pump 48, the valves 52, 54 and a valve 160 controlling the flow of rinsing and sheath liquid to the pipette 40, the valves 68, 56, 148, 146, 144, 114, 112, 102, 58, 108, 83, 162 and 116 as well as motors 62, 82, and 122 of pumps 60, 80, 120, respectively, and pumps 48, 140 is shown in FIG. 4 which illustrates a timing diagram of these elements when performing an operation of the type described above. The means for controlling the valves and motors according to the timing diagram are not shown in details and may be realised in several known ways, preferably through electronic circuitry e.g. a computer.

Figure 2:
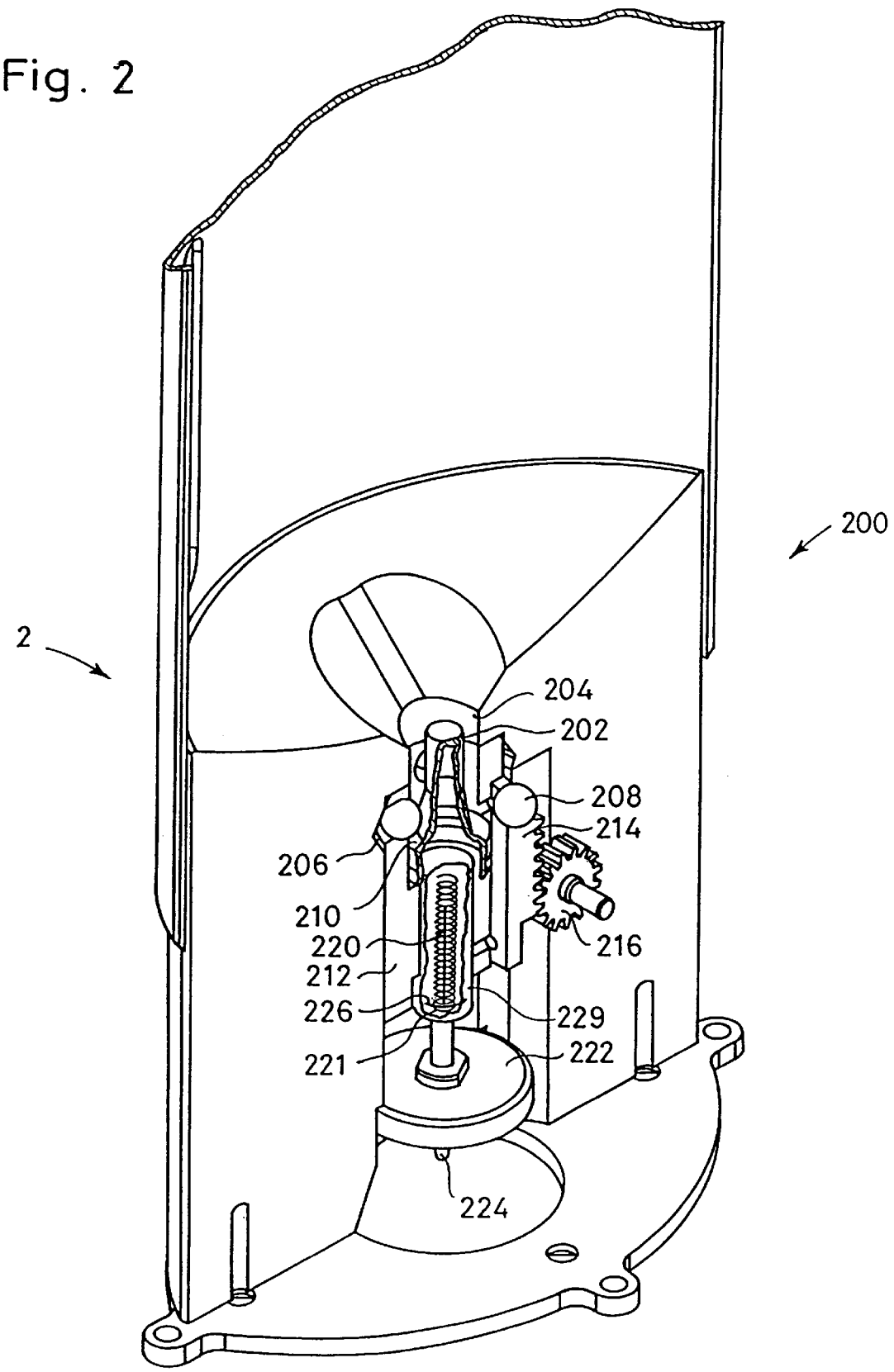
FIG. 2 illustrates a cross section of the presently preferred element 200 for introducing EB from the bag shown in FIG. 1 into the system.

FIG. 2 illustrates a cross section of the presently preferred element 200 for introducing EB from the bag illustrated in FIG. 1 into the system. It should be kept in mind that EB is mutagenic and potentially carciogenic whereby the handling of this chemical should take place with utmost care.

Of course, it is the concern of manufacturers of instruments of this type to ensure that the instrument does not cause laboratory personnel to be exposed directly to this chemical. In the present instrument, this is ensured by using infusion bags of the types typically used in hospital environments also for toxic chemicals. The advantage of this type of bag is that the liquid in the bag is always at ambient pressure so that no pressure equalization takes place when piercing the bag. Pressure equalization may otherwise cause the content to be splashed onto the surroundings and any personnel operating the elements. In addition, the apparatus illustrated in FIG. 2 ensures that the operator cannot come into contact with the needle piercing the EB bag as the needle is constantly either protected by a metal element or introduced into the bag.

In the actual embodiment, the bag (not shown on FIG. 2) is fitted with typical connecting piece 202 which fits into a hole 204 in the element 200. Inside the hole 204 at the opening thereof, a circular groove 206 is provided in order to receive three balls 208 when the connecting piece 202 is withdrawn from or introduced into the hole 204. The connecting piece 202 comprises a collar 210 which prevents the connecting piece 202 from being withdrawn from the hole 204 when the balls 208 are not received in the groove 206. The balls 208 are held in conical holes in a transporting device 212 so that they 208 cannot fall into the hole 204. The transporting device 212 is interconnected to a toothed rod 214 engaging with a tooth wheel 216 which is again connected to a handle (not shown). Turning the handle (not shown) will transfer the device 212 between an upper position wherein the balls 208 may be received in the groove 206 and a lower position which will be described below.

A hypodermic needle 220 for penetrating the bag (not shown in FIG. 2) in order to withdraw EB therefrom is rigidly interconnected to a bottom member 222 through which EB may be led to a connecting member 224 for connection with the liquid system of the rest of the apparatus.

Also connected to the bottom member 222 is a protecting cylinder 229 which is slidingly movable in relation to the needle 220. A member 226 is rigidly connected to a needle 220, and a compression spring 221 engages with the member 226 and an upper inner surface of the cylinder 229. Thus, when cylinder 229 is pressed towards the bottom of the hole 204, the needle 220 will be exposed as it is passed through a hole at the end of the cylinder 229. However, the cylinder 229 may only be displaced downwards by contact with the interconnecting member 210 which is connected to a bag (not shown). Thus, this position where the needle 220 may be exposed is the lower position of the member 212.

The movement of the cylinder 229 is independent of any movement of the element 212 as long as no fitting member 210 is introduced to engage therewith. Thus, independently of the position of the element 212, the needle 220 will always be protected by the cylinder 229 unless a fitting member 210 is introduced to press the cylinder 229 downwards.

Thus, the present element 200 will ensure that the EB contaminated needle is only exposed from the cylinder 229 when it is to be introduced into a connecting member 210 of a bag. This will prevent an operator of the instrument from getting into contact with the EB. Another advantage of using the bag illustrated in FIG. 1 is that the bag can be emptied almost totally, whereby waste of this very toxic EB is reduced to a minimum.

Figure 3:
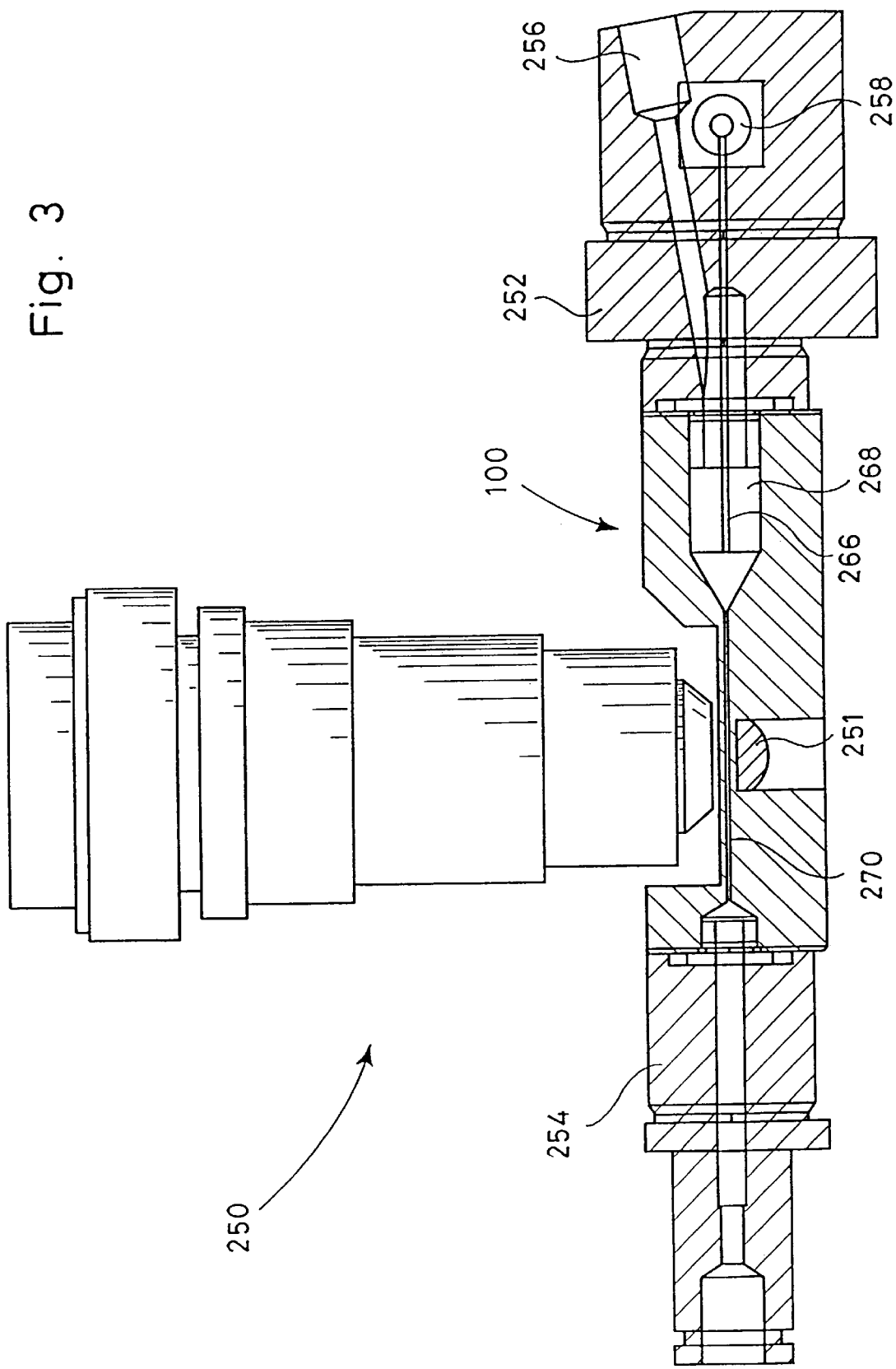
FIG. 3 is a cross sectional view of the measuring system of the apparatus illustrating the preferred sample cuvette, and part of the optical system used for detection of cells

FIG. 3 illustrates a part of the measuring setup at the cuvette 100 of FIG. 1. This measuring setup corresponds to a known epi-fluorescence measurement as described in Japanese published patent application with publication number 1-105136 for example. Light from e.g. a halogen lamp (not shown) is transferred through a heat filter (not shown) removing IR and UV light which might otherwise heat the rest of the system, and a bandpass filter (not shown) transmitting only light which excites the EB, diverted by a dichroic filter (not shown) toward focusing optics 250 focusing the radiation on to the very narrow liquid string or sheet comprising the EB stained cells passing through the cuvette 100. The fluorescence generated due to this illumination is subsequently collected by the same focusing optics 250 and is transmitted through the dichroic filter (not shown) and a filter (not shown) transmitting only fluorescence and launched onto a photo multiplier tube (not shown) which detects the fluorescence from each of the stained cells.

In FIG. 3 the optics for focusing the exciting light onto the string or sheet of liquid and for collecting the fluorescence is referred with numeral 250 and is usually a microscope objective.

In addition, the presently preferred cuvette furthermore comprises a curved mirror 251 positioned on the opposite side of the string or sheet of sample-dye mixture, compared to the optics 250, so as to reflect part of the fluorescence not directly collected by the optics 250. Naturally, this increases the total amount of fluorescence detected by the system. The preferred mirror 251 is a plano-convex lens which has been coated with a reflective coating on the spheric side and which is suitably fastened to the cuvette 100.

In FIG. 3, the cuvette 100 is shown interconnected with elements 252 and 254 for introducing liquids into and receiving liquids from the cuvette 100, respectively. In the element 252, the sheath fluid is introduced into path 256, and the mixture of milk and EB is introduced into the path 258. Path 258 is introduced into a hollow rod 266 forming part of the cuvette 100. The path 256 is introduced into the surroundings 268 of the rod 266. When transferring liquid through the paths 256 and 258, the shape of the cuvette 100 at the surroundings of the rod 266 will ensure that liquid flowing from the rod 266 will form a thin string in the narrow passage 270 of the cuvette 100 inside a sheath of fluid (from the container 132 comprising rinsing and carrier/sheath liquid). In the present example, the passage 270 has cross sectional dimensions of 200 µm×200 µm and the sample sheath therein has a width of approx. 20 µm.

This type of setup has the advantage that the focusing and collecting optics can be concentrated on an area having a diameter of approx. 100 µm (even though a diameter down to 20 µm may in principle be used). Impurities having a size of approx. 200 µm may be transferred through the system without causing clogging. Naturally, the presence of an impurity may cause an erroneous count in the system. This, however, is acceptable as the alternative is a system which may cease operation each time a large impurity clogs the cuvette.

When comparing the size of the test area (100 µm or down to 20 µm) to the diameter of white blood cells (leucocytes) in milk (5–15 µm) it is seen that this measuring technique may be extremely efficient.

FIG. 5 illustrates four graphs which are related to the function of the instrument. Each stained cell is detected in known manner as an electric pulse by the optical/electrical equipment described above. Each pulse is quantized i.e. digitized, to assign it to one of preferably 512 channels each representing a small interval of pulse voltage in known manner.

The pulse size distribution of a typical stained milk sample detected in a system as described above is illustrated in FIG. 5a). The cell counter instrument is associated with a digital signal processor, DSP, and an internal computer board, as well as an external computer such as a PC, arranged to calculate (and preferably comprising a monitor able to show) the pulse size distribution of each milk sample.

From this graph can be seen that a large amount of low energy pulses are detected (See arrow A). These low energy pulses are caused by noise and scatter as well as stray light, and should, thus, be eliminated from the measurement. In FIG. 5a) a top is seen (See arrow B) which represents the actual cells in the sample. Thus, in order to remove the noise and scattered light, a pulse energy threshold should be used. Preferably, a discriminator threshold is positioned in the minimum between the low energy pulses and the top representing the cells (See arrow C).

Another method of determining the position of this discriminator threshold is to fit a Gaussian curve to the top (arrow B) and an exponential curve to the part at arrow A. Subsequently, the threshold (arrow B) is positioned at the position where the residual area under these two curves is the same.

The apparatus described in the foregoing may perform the determination of the cell count according to a prior art routine for counting the number of cells in a sample. Such known measurement is proceeded for a fixed period of time, e.g. typically being in the order of 2 seconds, where the energies of the individual pulses are registered.

For each milk sample, the pulse energy distribution of the type seen in FIG. 5a) is determined, where from the energy (voltage) of the discriminator threshold of this measurement is calculated. Finally, the number of pulses having an energy higher than the discriminator threshold is determined, and the total number of cells per volume of the milk sample is calculated.

According to the present invention, this method may be improved by making the actual measuring time "dynamic", i.e. variable.

Obviously, the obtained cell count may be erroneous. The uncertainty of the measurement may be described by the Coefficient of Variation, CV. FIG. 5b) shows the CV versus the cell count, (i.e. the number of cells in a milk sample) detected for three different measuring times. Obviously, the uncertainty of a measurement is reduced when a larger volume of the sample has been used for the measurement (corresponding to a longer period of measuring time).

In the presently preferred embodiment, typically 1/300 ml sample is used in a measurement taking place in approx. 2 seconds. In the following, we will define the working factor (M) as the divisor defining the sample volume in ml (that part of a millilitre of a sample used in the measurement)—in the above example, the working factor (M) is 300. According to the invention, in the process of having a dynamic uncertainty, the working factor (M) is allowed to vary depending on the final determined number of cells (count) counted.

The relative standard deviation may be determined from:

$$CV = \sqrt{\frac{M}{\text{count}}}$$

From this it is seen that increasing the volume tested will decrease M and, thus, decrease CV.

From FIG. 5b), it may be seen that a given uncertainty may, of course, be obtained by simply allowing the measuring time to be long enough (the number of cells being large enough/the volume being large enough). However, it would drastically reduce the capacity of the instrument (number of samples tested per hour) if all samples would suddenly require a measurement time of maybe up to 7 times of that actually required by the majority of the samples in order to ensure an acceptable uncertainty for a few samples.

In order to attempt to maintain the capacity of the instrument or at least to minimize the reduction, two different methods of determination according to the invention have been developed as shown in FIGS. 5c and 5d.

In FIG. 5c), the graph of the uncertainty of one preferred embodiment of an apparatus and method according to the invention is disclosed. In this embodiment, the uncertainty of the measurement has been reduced in two areas along the cell number axis.

A method and apparatus of this type would be desired, if it was to be determined whether the number of cells in the sample was above and/or below each of a number of predetermined threshold values T1 and T2, e.g. grade limits decisive of the payment for raw milk received in a dairy. If the number of cells (the cell count) appears to be close to one of the threshold values, a smaller uncertainty is required in order to be able to perform the determination with a specific, desired CV, whereas a larger uncertainty would be acceptable, if the number of cells was far away from the important threshold values.

In a preferred embodiment the operator selects one or more 'grade limits' also called 'classification boundaries' and a desired probability of correct classification. In the following, an example of a measurement will be given in which the probability of correct classification is selected to be 95% (which corresponds to approximately 2 standard deviations) and wherein a classification boundary is selected at 200,000 cells/ml.

Performing the measurement in 2 seconds, the M will be 300 (cf. the above) whereby, $$CV_{200,000} = \sqrt{\frac{300}{200,000}} \cdot 100\% = 3.9\%$$

$$sd_{200,000} = CV_{200,000} \cdot \text{count} \sim 7,750$$

$$2 \cdot sd_{200,000} = 15,491 \sim 16,000$$

Thus, if the first estimate of the count is in the interval {(200,000−16,000)−(200,000+16,000)}={184,000−216,000} the measurement will continue so as to increase the volume and, thus, decrease M, so as to increase CV. If the count is outside this interval, the measurement is stopped.

If this intermediate prediction resulted in a number of cells (cell count) being within a certain distance from a threshold value (e.g. a grade limit), the measurement time will automatically be prolonged while new estimates are performed, until the estimates give cell counts outside the given boundary around the threshold values or until the uncertainty of the measurement was reduced to an acceptable limit.

Figure 7:
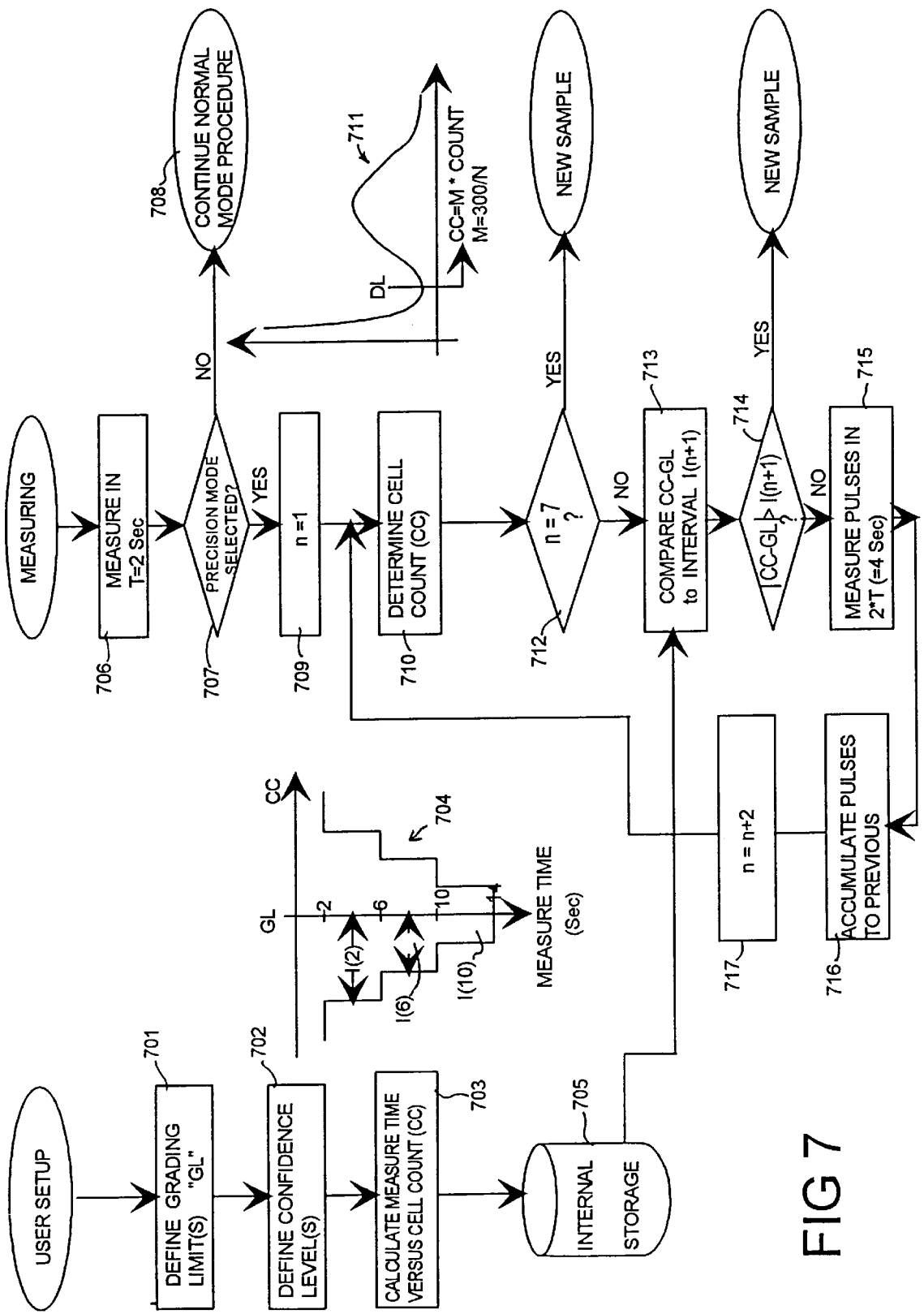

A presently preferred embodiment of the above described mode of operation is schematically shown in a diagram in FIG. 7. The steps 701–705 are preferably carried out in a personal computer forming the user interface. If the user has selected a precision mode the user sets the grading limits (step 701) and the confidence levels (step 702) on the keyboard of the personal computer. Then the necessary measure time versus cell count (CC) is calculated in step 703. A stepwise curve 704, as shown to the right of step 703, is obtained. The result is stored in an internal storage at step 705.

When a cell count of a milk sample is measured, the measuring starts by counting cells for 2 seconds (step 706) for example. If (step 707) the user has selected normal mode operation (step 708) the counting procedure stops, and a new sample will be measured. If (step 707) the user has selected a precision mode, the precision procedure will start by setting n=1 (step 709). The cell count is determined (step 710) from the pulse size distribution curve at step 711, which preferably is calculated in a DSP.

DL denotes a discriminator level which may be determined (in the DSP) as the minimum on the curve. The area to the right of the DL corresponds to the counted cells. The cell count (the number of cells in 1 ml)=M * count; M=300/n. The cell count, CC, minus the grade limit, GL, is compared to the interval l(n+1) (713) defined of the curve (704). If the distance between the cell count and the grading limit is greater than the interval l(n+1) from the step curve 704 the counting of the present sample is good enough and further counting is stopped. A new sample is then introduced in the cuvette of the cell counter. If (step 714) the distance between the cell count and the grading limit is smaller than the interval l(n+1) the counting of the present sample is continued in 4 sec. more (step 715). All registered pulses are accumulated (step 716) and a new cell count is calculated (step 710). The calculations may proceed for 14 seconds, corresponding to n=7 (step 712).

Preferably the above calculations are carried out in a computer board and a DSP (Digital Signal Processor) located in electronic circuitry behind the fluid system as well as a personal computer, connected by interfaces, all of which is well-known to people in the art, for which reason no further details are shown.

In FIG. 5(d), a second embodiment of the method or apparatus of the present invention is illustrated. In this apparatus and/or method, the measurements are performed at a given uncertainty. Due to the presently preferred upper limit of the measuring time of 14 seconds small numbers of cells (cell counts), of course, cannot be measured at this low uncertainty. However, when the graph representing the uncertainty of a 14-second measurement reaches the desired uncertainty, the uncertainty is kept at the same level until the 2-second graph automatically brings this uncertainty even lower, as 2 seconds is the presently preferred lower limit of measuring time. In this mode of the presently preferred apparatus, the operator typically pre-selects a maximum CV, whereby the apparatus will continue the measurement by decreasing M (increasing the volume used in the measurement), until the count determined and the M obtained give a satisfactory CV. However, as described above, it may be preferred to impose a maximum volume (minimum M), to be used in the measurement, on the apparatus so as to ensure a minimum throughput of samples. In the presently preferred apparatus, a minimum M=300/7≈43 is selected.

In the present instrument, the first predicted value is obtained after a measurement period of 2 seconds. Subsequently, 30 estimates are provided per second until an estimate gives a suitable probability of correct classification or a suitable CV, depending on the actual mode of the instrument. In the preferred embodiment of the present instrument, a maximum measurement time of 14 seconds is possible for each milk sample in a container 42. Obviously, this measurement time may be prolonged to any desired period of time.

Thus, in the new cell counter according to the invention, the capacity of the instrument is generally maintained close to the maximum capacity, which may be obtained with the fixed measurement time, typically 2 seconds in the present instrument. The advantage of the new counter is that the measurements can be obtained with a better (smaller) uncertainty if necessary, only sacrificing a minor portion of the maximum capacity of the instrument.

Generally, the present method may, provide both better and faster results as a large part of the measurements may be performed faster than with the prior art instrument (with a lower but still acceptable uncertainty) and only a few measurements will be slower (but then with a better uncertainty than the prior art instrument).

The apparatus according to the invention comprises a liquid flow system as shown in FIG. 1 and described in the foregoing, allowing the measurement sequence to be interrupted as soon as the calculating means decide that the uncertainty of the actual cell count is small enough to rely on the present determination. The apparatus will then be ready to carry on with the next sample, thereby maintaining a high capacity while obtaining reliable cell counts.

We claim:

1. A method of determining the number of particles or cells in a liquid sample, the method comprising:
    a) determining the number of particles or cells in a first volume of the liquid sample,
    b) determining the statistical uncertainty of the determined number of particles in said first volume,
    c) if the determined uncertainty is larger than a predetermined value, determining the number of particles or cells in a further volume of the liquid sample, d) adding the numbers of cells or particles determined in steps a) and c), e) determining the statistical uncertainty of the number of particles determined in step d), f) repeating steps d) and e) with at least one further volume of the liquid sample, until the uncertainty determined in step e) is lower than said pre-determined value or until a pre-determined total volume of the liquid sample in which the number of cells or particles has been determined exceeds a predetermined volume larger than said first volume.

2. A method according to claim 1, wherein the number of cells or particles in the first and subsequent volumes is determined by flowing said volumes past a detector detecting the presence of the cells or particles.

3. A method according to claim 2, wherein the cells or particles are stained with a fluorescing agent and irradiated with radiation exciting said fluorescing agent, and where the detector detects the presence of the particles or cells by detecting the fluorescence emitted from said excited agent.

4. A method according to claim 3, wherein the irradiation with radiation exciting said agent and the emission of said fluorescence takes place while the irradiated cells or particles are held by a cuvette made of a material transmitting said radiation and said fluorescence.

5. A method according to claim 4, wherein the number of cells or particles of said first and at least one subsequent volume of the liquid sample is determined while said first volume and said at least one subsequent volume of sample are flowing through said cuvette.

6. A method according to claim 5, wherein the liquid sample flows in a single string or layer surrounded by a sheath fluid inside the cuvette.

7. A method according to claim 1, wherein the detector detects the presence of the cells or particles by detecting a difference in the electrical conductivity of the volumes flowing past the detector.

8. A method according to claim 1, wherein the determination of the number of particles or cells in the first and subsequent volumes comprises an assay step which is based on the quantification of a target molecule or of a molecular interaction involving a target molecule, the interaction itself or a product thereof being detectable and being correlated to the number of cells or particles in the volumes.

9. A method according to claim 8, comprising a colouring agent colouring the cells or particles and wherein the determination of the number of cells or particles in the volumes is performed by determining the coloration of the volumes.

10. A method according to claim 8, wherein the cells or particles and an agent take part in an antigen/antibody reaction.

11. A method according to claim 10, wherein the agent, having taken part in the antigen/antibody reaction, is able to direct a chemical reaction in the volumes.

12. A method according to claim 11, wherein the agent comprises an enzyme, wherein the chemical reaction is the enzymatic splitting of a reagent, and wherein concentrations of any reaction products from the enzymatic splitting of the reagent relate to the number of cells or particles in the volumes.

13. A method according to claim 1, wherein said pre-determined value is independent of the determined number of cells or particles.

14. A method according to claim 1, wherein the liquid sample is a sample of milk or a milk product and wherein the agent is Ethidium Bromide.

15. A method according to claim 1, wherein said pre-determined value depends on the determined number of cells or particles.

16. A method according to claim 15, wherein said pre-determined value is reduced in pre-determined intervals of numbers of cells or particles.

17. A method according to claim 16, wherein the intervals are defined by an upper and lower cell or particle number, each being in the interval, where the reduced pre-determined value is reduced at least 10% compared to that of the cell or particle numbers adjacent to said upper and lower cell or particle numbers and outside said interval.

18. A method according to claim 17, wherein the reduced pre-determined value is reduced at least 20%.

19. A method according to claim 18, wherein the reduced pre-determined value is reduced at least 30%.

20. A method according to claim 19, wherein the reduced pre-determined value is reduced at least 40%.

21. A method according to claim 20, wherein the reduced pre-determined value is reduced at least 50%.

22. An apparatus for determining the number of particles or cells in a liquid sample, said apparatus comprising:

means for determining the number of particles or cells in a first and at least one further volume of the liquid sample, means for determining the statistical uncertainty of the determined number of particles or cells in a given volume of said liquid sample, means for determining whether the determined uncertainty is lower than a pre-determined value, and means for adding the numbers of particles or cells determined in said first and said further volumes of said liquid sample.

23. An apparatus according to claim 22, further comprising means for holding the first and at least one subsequent volume of the sample during the determination of the number of cells or particles therein.

24. An apparatus according to claim 23, wherein the holding means comprise means for detecting variations in the electrical conductance of the volumes therein.

25. An apparatus according to claim 22, wherein the means for determining the number of cells or particles in said first and subsequent volume(s) of sample comprise:

means for mixing at least part of the liquid sample with a volume of a dye so as to stain the cells or particles with a fluorescing agent, means for irradiating said stained cells or particles with radiation exciting said fluorescing agent, and means for detecting fluorescence emitted from stained cells or particles having been irradiated with said exciting radiation.

26. An apparatus according to claim 25, wherein the holding means comprise a cuvette receiving and transmitting the exciting radiation and said fluorescence.

27. An apparatus according to claim 22, further comprising means for storing a number of pre-determined values and means for selecting a pre-determined value depending on the determined number of cells or particles determined in the liquid sample.

28. An apparatus according to claim 27, further comprising a mixing means connected to a concentrated dye container and a dilute container and having an exit from which a diluted dye is output.

29. An apparatus according to claim 28, wherein the concentrated dye container is a resilient container.

30. An apparatus according to claim 22, further comprising waste means for receiving the mixture of dye and liquid sample subsequent to the determination of the number of cells or particles in a volume of the sample.

31. An apparatus according to claim 30, wherein the waste means comprise at least two containers for receiving different parts of the mixture, a first container for receiving parts of the mixture where the concentration of dye is lower than a pre-selected concentration and a second container for receiving parts of the mixture where the concentration of dye is higher than the pre-selected concentration.

32. An apparatus according to claim 22, further comprising waste means for receiving parts of the liquid sample not having been mixed with the dye.

* * * * *